United States Patent [19]

Sakata et al.

[11] Patent Number: 5,618,733
[45] Date of Patent: Apr. 8, 1997

[54] REAGENT FOR ANALYZING LEUCOCYTES

[75] Inventors: Takashi Sakata; Takashi Morikawa; Kinya Uchihashi, all of Kakogawa; Tomomi Hashimoto, Kobe, all of Japan

[73] Assignee: Toa Medical Electronics Co., Ltd., Japan

[21] Appl. No.: 360,005

[22] Filed: Dec. 20, 1994

[30] Foreign Application Priority Data

Dec. 22, 1993 [JP] Japan .................................. 5-324860

[51] Int. Cl.$^6$ .................................................. G01N 33/52
[52] U.S. Cl. .................................. 436/17; 436/63; 435/2; 435/7.25; 424/533; 424/534
[58] Field of Search ................... 436/17, 18, 10, 436/63, 164, 172, 900; 422/77; 435/2, 7.25; 424/529–534

[56] References Cited

U.S. PATENT DOCUMENTS

| | | | |
|---|---|---|---|
| 4,483,928 | 11/1984 | Suzuta et al. | 436/519 |
| 5,155,044 | 10/1992 | Ledis et al. | 436/17 |
| 5,175,109 | 12/1992 | Sakata et al. | 436/17 |
| 5,179,026 | 1/1993 | Matsuda et al. | 436/63 |
| 5,196,346 | 3/1993 | Lefevre et al. | 436/63 |
| 5,227,304 | 7/1993 | Wong | 436/17 |
| 5,242,832 | 9/1993 | Sakata | 436/17 |
| 5,250,437 | 10/1993 | Toda et al. | 436/10 |
| 5,250,438 | 10/1993 | Ryan | 436/17 |
| 5,350,695 | 9/1994 | Colella et al. | 436/63 |
| 5,378,633 | 1/1995 | von Behrens et al. | 436/63 |

FOREIGN PATENT DOCUMENTS

| | | |
|---|---|---|
| 0430750 | 6/1991 | European Pat. Off. . |
| 0442776 | 8/1991 | European Pat. Off. . |
| 0444241 | 9/1991 | European Pat. Off. . |
| 0598663 | 5/1994 | European Pat. Off. . |
| 62-71857 | 4/1987 | Japan . |
| 1-502931 | 10/1989 | Japan . |
| 3-266999 | 11/1991 | Japan . |

OTHER PUBLICATIONS

Patent Abstracts of Japan, vol. 15, No. 144 (P–1189).

*Primary Examiner*—James C. Housel
*Assistant Examiner*—Rachel Heather Freed

[57] ABSTRACT

A reagent for analyzing leucocytes comprises (a) at least one ionic surfactant, being either a cationic or an amphoteric surfactant, in an amount sufficient for lysing erythrocytes and causing damage to a part of cell membranes of leucocytes; (b) at least one organic compound having a hydrophobic group and an acidic group which has a negative charge in an aqueous solution in an amount sufficient for a preserving leucocyte morphology by combining with a cationic component in leucocytes; (c) a nonionic surfactant; and (d) a buffer for adjusting pH.

28 Claims, 12 Drawing Sheets

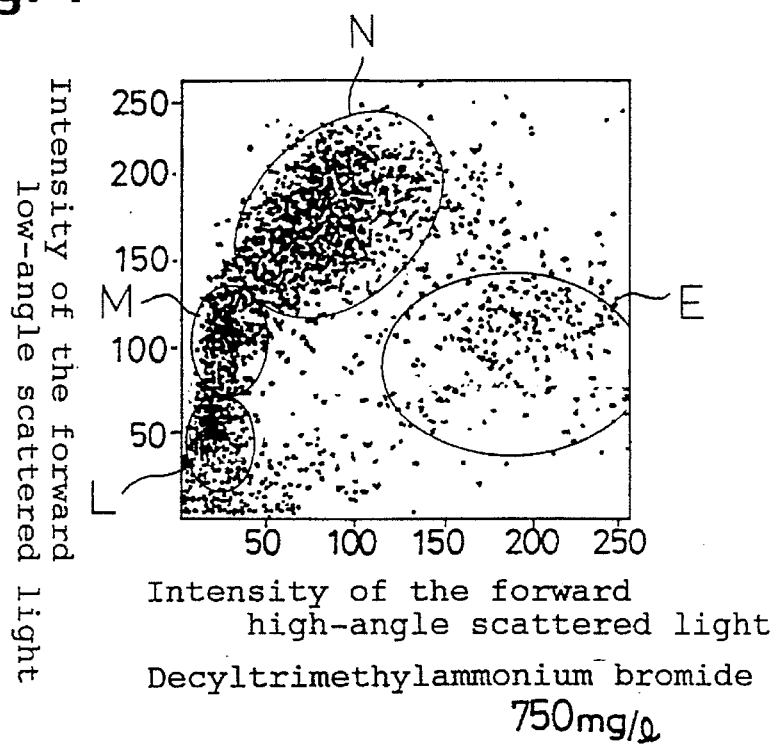
Fig. 1 Decyltrimethylammonium bromide 750mg/ℓ
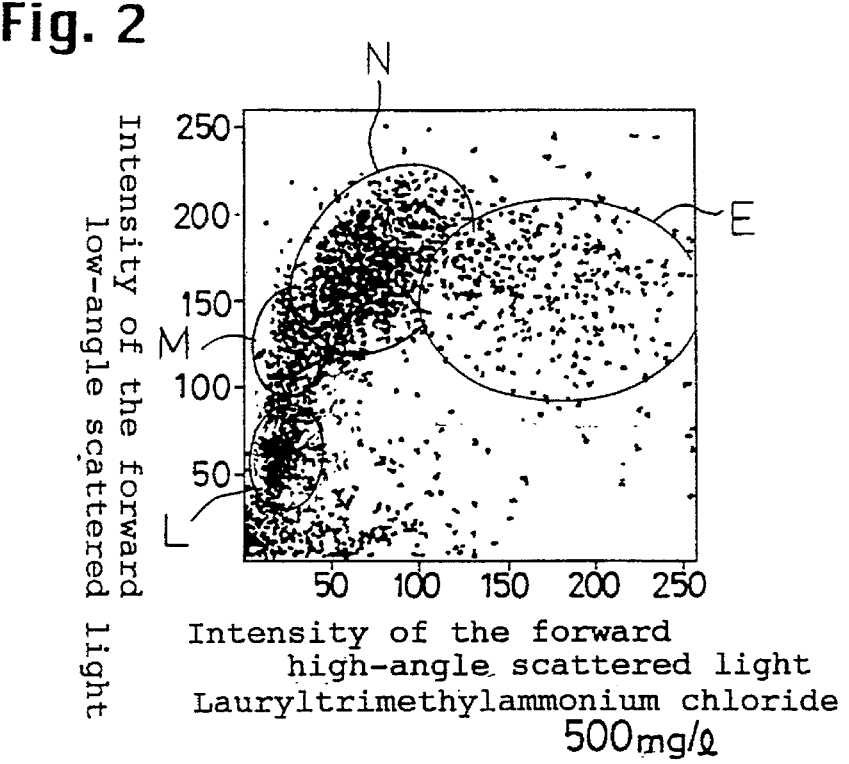
Fig. 2 Lauryltrimethylammonium chloride 500mg/ℓ

Alizarin Violet 3R
3g/ℓ

Alphazurine A
0.3g/ℓ

Guinea Green B
0.3g/ℓ

Alizarin Yellow-R
0.3g/ℓ

Ethyl alcohol 50 mℓ/ℓ

2-Propanol 25 mℓ/ℓ

2-Phenoxyethanol
2.5 mℓ/ℓ

MES (PH5.5)

HEPES (PH 7.0)

TRIS (PH 8.5)

BC-25TX 3.0g/l

BC-25TX 2.0g/l + HCO-60 1.0g/l

REAGENT FOR ANALYZING LEUCOCYTES

BACKGROUND OF THE INVENTION

1. Field of the Invention

The present invention relates to a reagent for analyzing leucocytes, especially for classifying and counting leucocytes using a classifying apparatus for leucocytes in the field of a clinical test.

2. Description of the Prior Art

In the field of a clinical test, it is important for the diagnosis of various diseases to classify and count leucocytes using the whole blood of patients.

For such a purpose, many apparati and methods have been reported.

In those apparati, leucocytes are classified into their subgroups (lymphocytes, monocytes, neutrophils, eosinophils and basophils) by the difference of RF signal intensity (changes in electric impedances at high-frequency), DC signal intensity (changes in direct current caused by the difference in the electroconductivity between the suspended particles and the liquid medium in which the particles are suspended), intensity of fluorescence, intensity of scattered light, absorbance, depolarization of scattered light or the like. In the classification and counting of leucocytes, it is necessary to pretreat the blood and lyse the erythrocytes so that the difference among each subgroup of the leucocytes according to the above-mentioned parameters can be detected.

For such a purpose, for example, leucocytes are shrunk to a suitable size using a lysing agent or specific cells are stained. The lysing agent used in shrinking leucocytes is an organic carboxylic acid, organic sulfonic acid or phenol (WO88/07187), or two kinds of cationic surfactants (WO 84/03771 and WO 84/02777). Examples of methods for lysing erythrocytes and staining specific cells are a method in which the blood is treated with a reagent comprising the combination of an erythrocyte lysing agent (saponin and/or sodium dodecylsulfate), a tertiary or quaternary ammonium salt, an alcohol, a polyoxyethylene sorbitan ester, glutaraldehyde or formaldehyde, alkylene glycol, a physiological salt and Chlorazol Black (Japanese Laid-Open Patent Publication Hei-03/266999 (corresponding to: FR8915166)) and a method in which blood is treated with a reagent comprising the combination of sodium dodecylsulfate, formaldehyde, sugar (or sugar alcohol) and a buffer, followed by subjecting to a peroxidase staining (Japanese Laid-Open Patent Publication Sho-62/071857 (corresponding to: U.S. Pat. Nos. 4,801,549 and 4,978,624)).

In the above-mentioned WO 84/03771 and WO 84/02777, the classification and counting of leucocytes are carried out by means of the difference in the DC signal intensity, which is convenient but has a disadvantage that leucocytes can be only classified into three subgroups.

Methods according to Japanese Laid-Open Patent Publication Sho-62/071857 and Hei-03/266999 can classify leucocytes into four or more subgroups, but require a treatment at a high temperature and a fixation using a toxic aldehyde.

Further, in the method of WO88/07187, leucocytes are detected by means of a RF signal, DC signal or the intensity of scattered light which has, however, a drawback in that the detectors are complicated, large in size and expensive.

SUMMARY OF THE INVENTION

An object of the present invention is to offer a reagent which can classify leucocytes at least into four subgroups using an inexpensive and simple apparatus, and without using such toxic agents as aldehydes.

The present invention provides a reagent for analyzing leucocytes comprising (a) at least one ionic surfactant in an amount sufficient for lysing erythrocytes and causing damage to a part of cell membranes of leucocytes; (b) at least one organic compound having an anionic group in an amount sufficient for making a morphological difference among leucocytes by combining with a cationic component in leucocytes; (c) a nonionic surfactant; and (d) a buffer for adjusting pH.

BRIEF DESCRIPTION OF THE DRAWINGS

FIG. 1 is a scattergram showing the intensity of forward low-angle scattered light and the intensity of forward high-angle scattered light measured with the reagent for analyzing leucocytes of the present invention which uses decyltrimethylammonium bromide as an ionic surfactant.

FIG. 2 is a scattergram showing the intensity of forward low-angle scattered light and the intensity of forward high-angle scattered light measured with the reagent for analyzing leucocytes of the present invention which uses lauryltrimethylammonium chloride as an ionic surfactant.

DETAILED DESCRIPTION OF THE PREFERRED EMBODIMENTS

Figure 3:
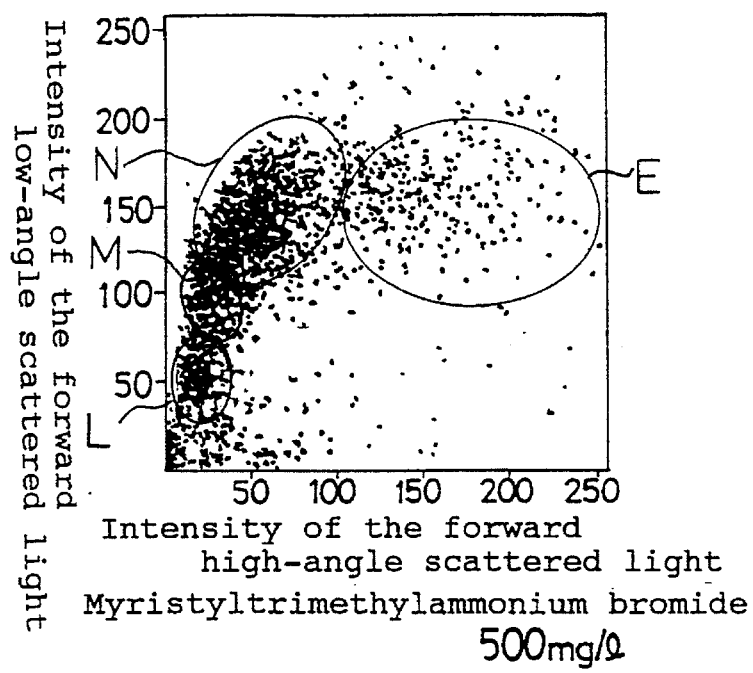
FIG. 3 is a scattergram showing the intensity of forward low-angle scattered light and the intensity of forward high-angle scattered light measured with the reagent for analyzing leucocytes of the present invention which uses myristyltrimethylammonium bromide as an ionic surfactant.
Figure 4:
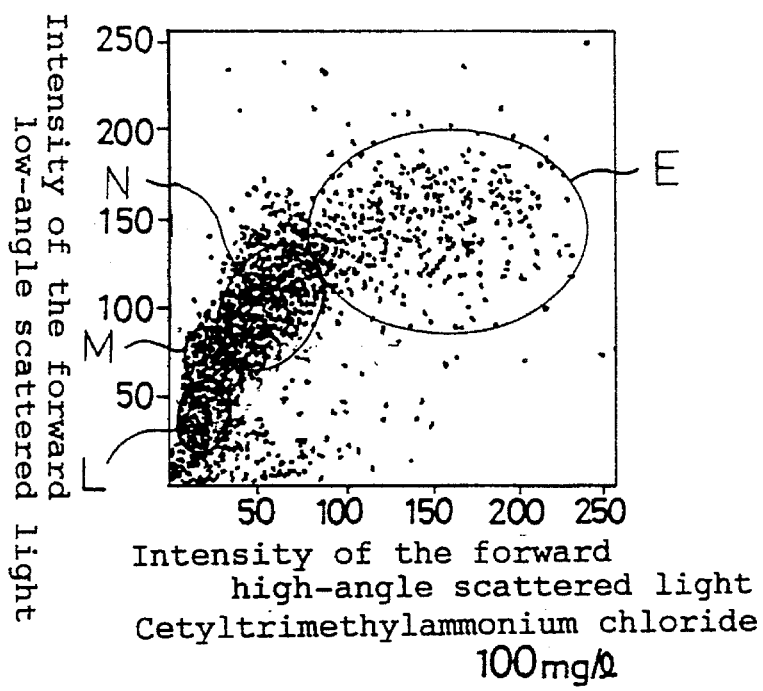
FIG. 4 is a scattergram showing the intensity of forward low-angle scattered light and the intensity of forward high-angle scattered light measured with the reagent for analyzing leucocytes of the present invention which uses cetyltrimethylammonium chloride as an ionic surfactant.
Figure 5:
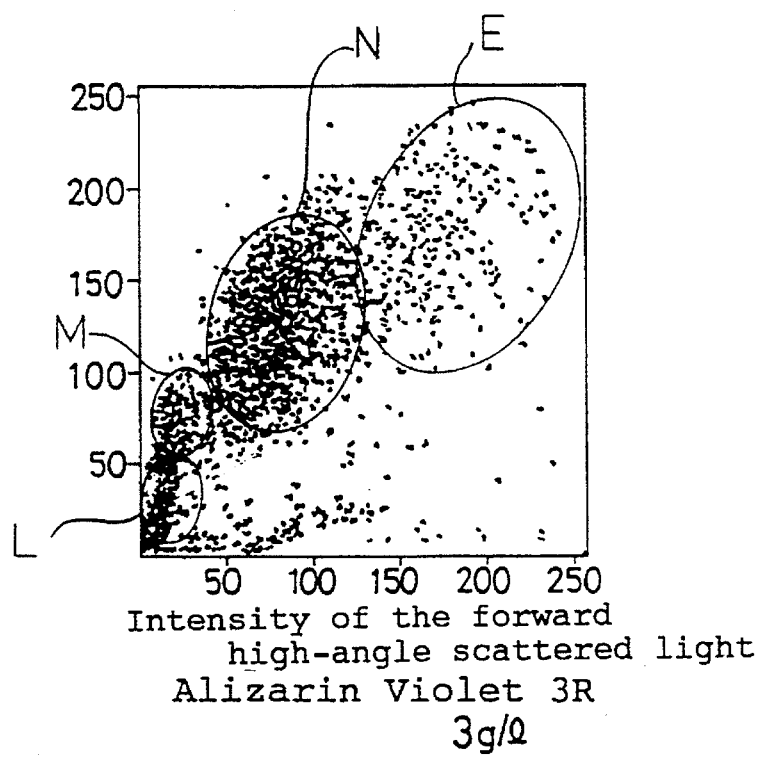
FIG. 5 is a scattergram showing the intensity of forward low-angle scattered light and the intensity of forward high-angle scattered light measured with the reagent for analyzing leucocytes of the present invention which uses Alizarin Violet 3R as an organic compound.
Figure 6:
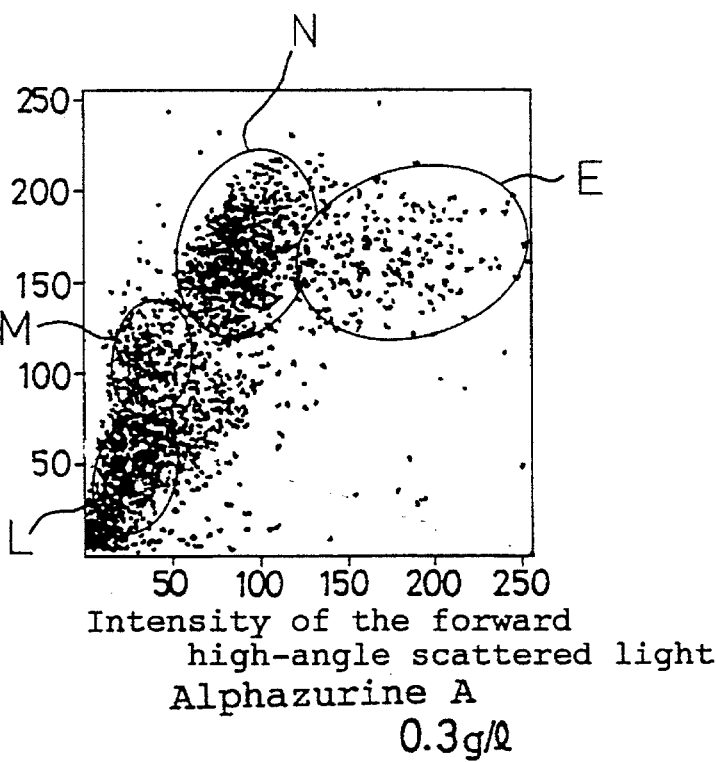
FIG. 6 is a scattergram showing the intensity of forward low-angle scattered light and the intensity of forward high-angle scattered light measured with the reagent for analyzing leucocytes of the present invention which uses Alphazurine A as an organic compound.
Figure 7:
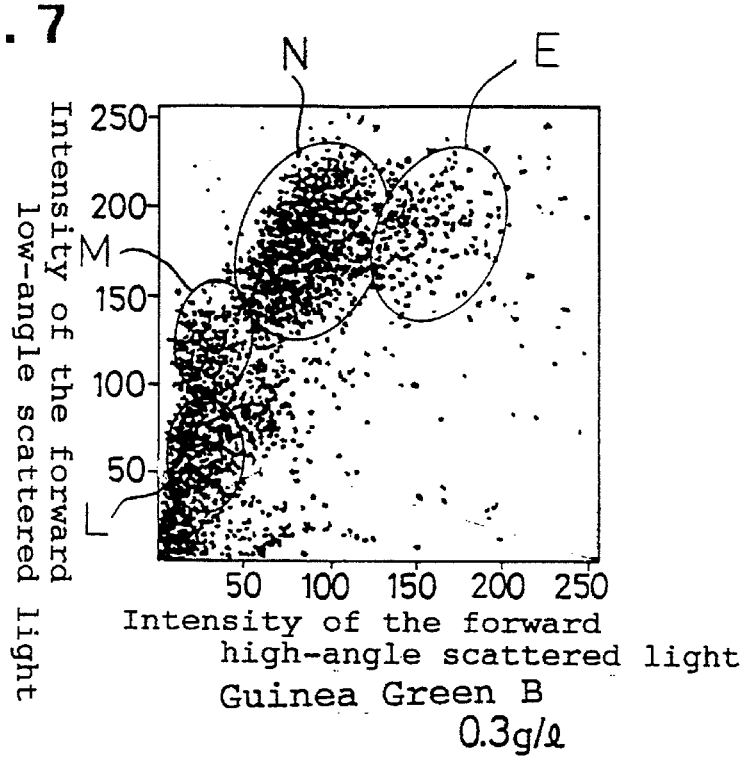
FIG. 7 is a scattergram showing the intensity of forward low-angle scattered light and the intensity of forward high-angle scattered light measured with the reagent for analyzing leucocytes of the present invention which uses Guinea Green B as an organic compound.
Figure 8:
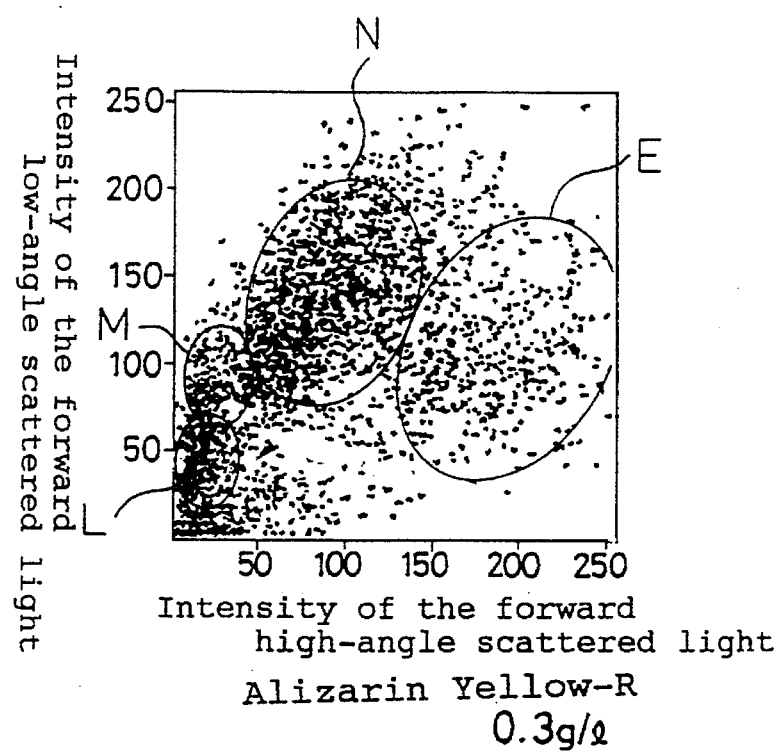
FIG. 8 is a scattergram showing the intensity of forward low-angle scattered light and the intensity of forward high-angle scattered light measured with the reagent for analyzing leucocytes of the present invention which uses Alizarin Yellow-R as an organic compound.
Figure 9:
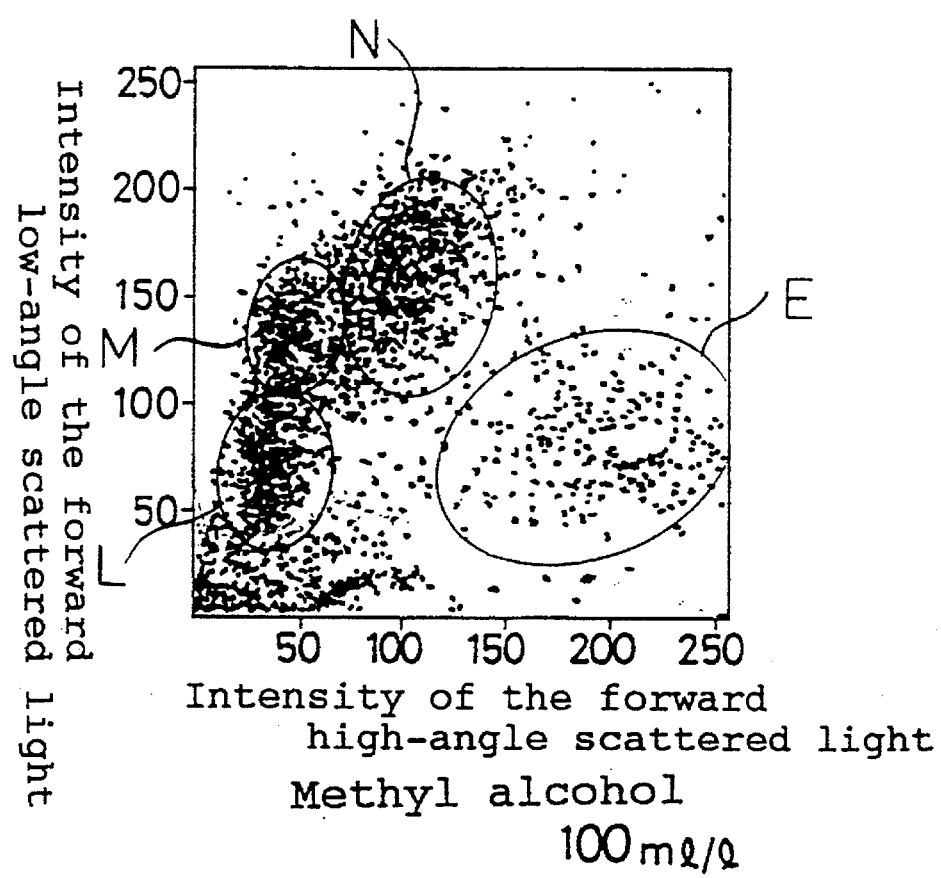
FIG. 9 is a scattergram showing the intensity of forward low-angle scattered light and the intensity of forward high-angle scattered light measured with the reagent for analyzing leucocytes of the present invention which uses methyl alcohol as an alcohol.
Figure 10:
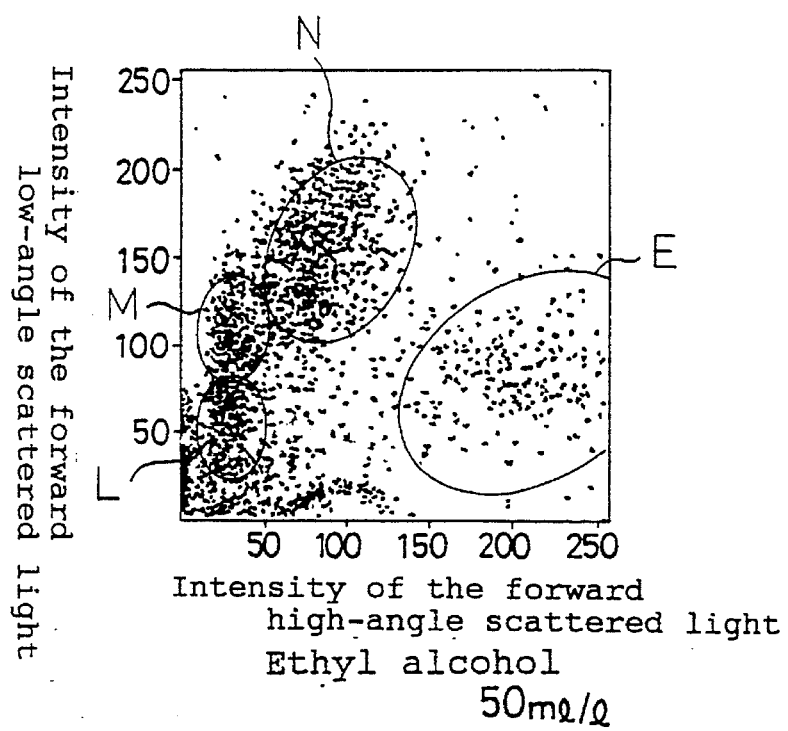
FIG. 10 is a scattergram showing the intensity of forward low-angle scattered light and the intensity of forward high-angle scattered light measured with the reagent for analyzing leucocytes of the present invention which uses ethyl alcohol as an alcohol.
Figure 11:
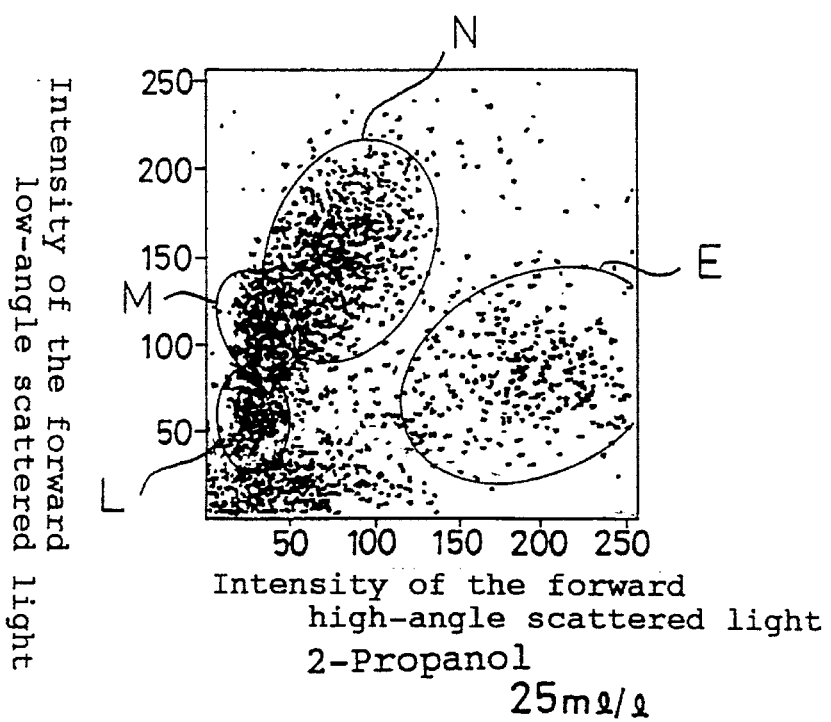
FIG. 11 is a scattergram showing the intensity of forward low-angle scattered light and the intensity of forward high-angle scattered light measured with the reagent for analyzing leucocytes of the present invention which uses 2-propanol as an alcohol.
Figure 12:
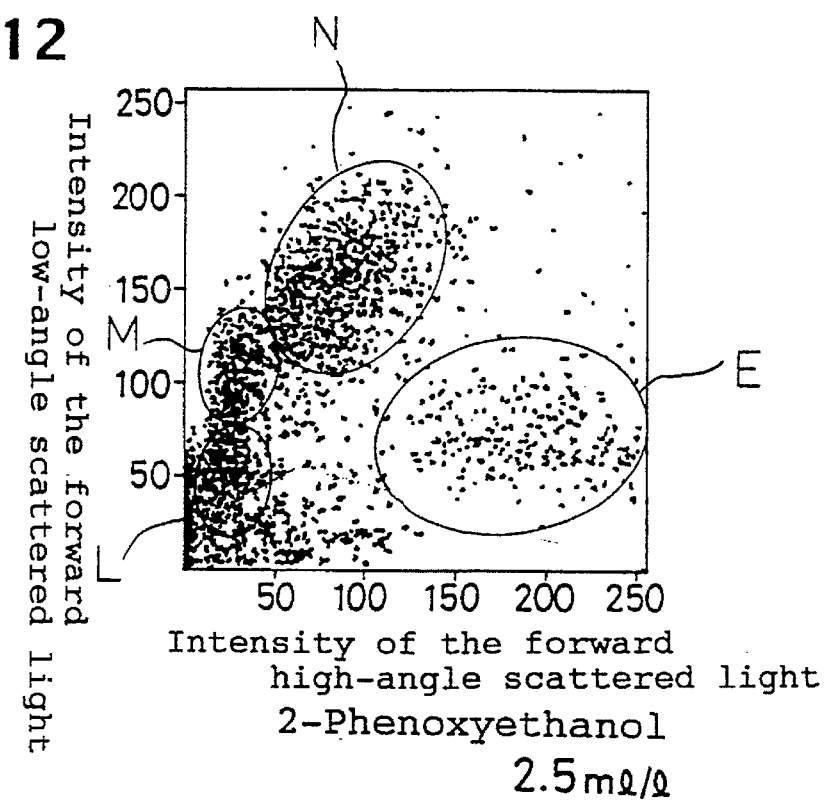
FIG. 12 is a scattergram showing the intensity of forward low-angle scattered light and the intensity of forward high-angle scattered light measured with the reagent for analyzing leucocytes of the present invention which uses 2-phenoxyethanol as an alcohol.

The ionic surfactant in the reagent for analyzing leucocytes in accordance with the present invention comprises at least one cationic surfactant or amphoteric surfactant.

Preferred cationic surfactants are those of the quaternary ammonium salt type or pyridinium salt type. The quaternary ammonium salt type and pyridinium salt type surfactants can be represented by the formulae;

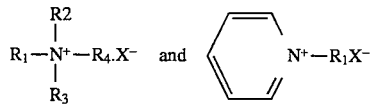

($R_1$ is a $C_{6-18}$ alkyl or alkenyl group; $R_2$ and $R_3$ are $C_{1-4}$ alkyl or alkenyl groups; $R_4$ is a $C_{1-4}$ alkyl or alkenyl group, or benzyl group; and X is a halogen atom). The total number of carbon atoms in the above formulae are preferably in the range of 9–30.

Examples of the $C_{6-18}$ alkyl or alkenyl group for $R_1$ are hexyl, octyl, decyl, dodecyl or tetradecyl, or hexenyl, heptenyl or octenyl; preferably, a linear alkyl such as octyl, decyl or dodecyl. Examples of the $C_{1-4}$ alkyl or alkenyl groups for $R_2$ and $R_3$ are methyl, ethyl, propyl or butyl, or propenyl; preferably, a $C_{1-3}$ alkyl such as methyl, ethyl or propyl. Examples of the $C_{1-4}$ alkyl and alkenyl groups for $R_4$ are methyl, ethyl, propyl or butyl, or propenyl; preferably, methyl, ethyl or propyl.

The amphoteric surfactant can be represented by the following formula;

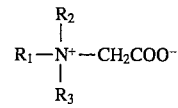

($R_1$, $R_2$ and $R_3$ are the same as defined above).

The total number of carbon atoms in the above three formulae are preferably in the range of 9–30.

The above-mentioned ionic surfactant is used in a sufficient amount to lyse erythrocytes and cause damage to a part of cell membranes of leucocytes. Specifically, it is suitable to use about 30–5,000 mg/liter of the total volume of the reagent, preferably about 50–3,000 mg/liter or, more preferably about 100–2,000 mg/liter, though it can be suitably modified depending upon the type of surfactant used or the like. Suitable amounts (concentrations) for each of the ionic surfactants in the reagent are given in Table 1. The ionic surfactant may be used singly or in a combination of two or more surfactants.

TABLE 1

| Surfactant | Amount (mg/liter) |
|---|---|
| Octyltrimethylammonium bromide (OTAB) | 1000–5000 |
| Decyltrimethylammonium bromide (DTAB) | 200–3000 |
| Lauryltrimethylammonium chloride (LTAC) | 150–2000 |
| Myristyltrimethylammonium bromide (MTAB) | 100–1500 |
| Cetyltrimethylammonium chloride (CTAC) | 50–1000 |
| Stearyltrimethylammonium bromide | 50–500 |
| Cetyldimethylethylammonium bromide | 50–500 |
| Laurylpyridinium chloride | 50–500 |
| Lauryldimethylaminoacetic acid betaine | 500–3000 |
| Stearyldimethylaminoacetic acid betaine | 500–3000 |

The ionic surfactant is required to possess a hemolytic activity of such an extent that it makes pores in cell membranes of leucocytes which can pass an organic compound as discussed later, but is not sufficiently potent to make the cell nuclei naked. As the ionic surfactants, conventional cationic surfactants (e.g., LTAC, MTAB and CTAC) are usable but are used in far smaller amount than an amount for making the cell nuclei naked so as to inhibit their own hemolytic activities. An ionic surfactant possessing low hemolytic activity is also usable because it is sufficient to disrupt a part of the cell membrane. The hemolytic activity of the ionic surfactant is in proportion to the number of carbon atoms of the hydrophobic group and, the more the number of carbon atoms, the more the hemolytic activity, therefore cationic surfactants having a low hemolytic activity such as DTAB and OTAB, or amphoteric surfactant are preferably used.

In addition to the ionic surfactant, the reagent in accordance with the present invention contains an organic compound having an anionic group which makes a morphological difference among leucocytes by combining with a cationic component in leucocytes. Specifically, the organic compounds have a hydrophobic group and an acidic group (ananionic group such as a carboxyl group, a sulfonic acid group, etc.) which has a negative charge in an aqueous solution, contain at least six carbon atoms and can combine with leucocytes, thereby modifying the shape of leucocytes. They are not particularly limited but nearly all kinds of acidic dyes can be used. Further, because there is no necessity of measuring the absorbance and the fluorescence intensity, other organic compounds other than dyes are applicable as well. Examples of the acidic dyes are Amido Black [Colour Index No. 20470], Alizarin Cyanine Green F [CI No. 61570], Acid Green 27 [CI No. 61580], Acid Blue 62 [CI No. 62045], Direct Red 31 [CI No. 29100], Brilliant Sulphaflavine [CI No. 56205], Alizarin Yellow R [CI No. 14030], Acid Blue 129 [CI No. 62058], Acid Green 25 [CI No. 61570], Chromotrope 2R [CI No. 16570], Coomassie Brilliant Blue R-250 [CI No. 42660], Carmine Acid [CI No. 75470], Coomassie Brilliant Blue G-250 [CI No. 42655], Carmoisine B [CI No. 14720], Direct Blue 86 [CI No. 74180], Ethyl Red [2-(4-diethylaminophenylazo)benzoic acid], Para Rosaniline [CI No. 42500], Violamine R [CI No. 45190], Acid Yellow 34 [CI No. 18890], Acid Orange 51 [CI No. 26550], Brilliant Crocein MOO [CI No. 27290], Guinea Green B [CI No. 42085], Acid Blue 29 [CI No. 20460], Rhodamine B [CI No. 45170], Sulforhodamine B [CI No. 45100], Lissamine Green B [CI No. 44090], Acid Blue 9 [CI No. 42090], Fast Green FCF [CI No. 42053], Azocarmine B [CI No. 50090], Aniline Blue [CI No. 42780], Alphazurine A [CI No. 42080], Alizaline Violet 3R [CI No. 61710], Acid Blue 41 [CI No. 62130], Bieblich Scarlet [CI No. 26905], Erythrosin B [CI No. 45430], Methyl Red [CI No. 13020], Methyl Orange [CI No. 13025], Orange I [CI No. 14600], etc. Examples of the organic compounds other than dyes are aromatic organic acids having a hydrophobic group and an acidic functional group or acids having a hydrocarbon of at least six carbon atoms or having a heterocylic ring. More specifically, examples of useful organic compounds other than dyes are 8-anilino-1-naphthalenesulfonic acid, 6-(p-toluidino)-2-naphthalenesulfonic acid, chromotropic acid, phthalic acid or naphthalenesulfonic acid, or their corresponding salts. The amount of such organic compound may be suitably chosen, depending upon the type of surfactant used or the like and is preferably, about 50–5,000 mg/liter of the total volume of the reagent or, more preferably about 100–3,000 mg/liter.

The reagent in accordance with the present invention further contains a nonionic surfactant. There is no particular limitation upon the nonionic surfactant and nearly all kinds of nonionic surfactants usually used as solubilizers may be used. Examples are nonionic surfactants having polyoxyethylene glycol (POE), polypropylene glycol (POP) or a block copolymer of polyoxyethylene glycol-polypropylene glycol (POE-POP) as a hydrophilic component. When only one kind of nonionic surfactant is used, it may cause a side effect of solubilizing leucocytes in addition to the desired lysis of an insoluble substance formed between the ionic surfactant with a cell-constituting component in erythrocytes. In such a case, it is preferable to use a combination of two or more nonionic surfactants such as those wherein the additional mole number of the hydrophilic groups are different. Alternatively, the combined use of nonionic surfactants wherein the structures of the lipophilic groups are different can inhibit the side effect. The amount of the nonionic surfactant which is necessary for dissolving the insoluble substance varies depending upon the type of ionic surfactant used or the like and is generally in the range of about 0.5–10 g/liter of the total volume of the reagent, preferably about 1–8 g/liter.

The reagent in accordance with the present invention further contains a buffer for adjusting pH. Usually, there is no particular limitation for the buffer so far as it is used for keeping pH constant and any buffer having a pKa of "a desired pH ±2.0" may be used. Examples are MES, TRIS, HEPES, succinic acid, phthalic acid or citric acid buffers. In the present invention, it is preferable to adjust the pH of the reagent to about 5–11 whereby the amount of buffer used is around 5–100 mM for the reagent.

An alcohol may be further used in the reagent without particular limitation. Preferable alcohols are those easily available at low cost on an industrial scale, such as alkanols (e.g. methyl alcohol and ethyl alcohol) and alcohols having an aromatic ring (e.g. phenethyl alcohol and 2-phenoxyethanol). With respect to its amount, about 5–20% with respect to the entire amount of the reagent is preferable in the case of methanol and a very rough yardstick is that, when there is an increase of one carbon, the amount is preferably halved. In the case of 2-phenoxyethanol, the preferred amount is 0.05–1%.

A metal salt may be added in the reagent. Preferred examples thereof are alkali metal salts such as sodium chloride, potassium chloride and lithium chloride. Usually, it is not necessary to use the alkali metal salt but, in the case of an apparatus wherein the measurement is conducted using a signal of electric resistance as mentioned later, the alkali metal is needed to adjust the electroconductivity of the sample to a value which is suitable for the measurement. The preferred amount in such a case is in the amount providing an electroconductivity of the solution of about 5–20 mS/cm.

The reagent for analyzing leucocytes in accordance with the present invention may be composed of two liquids comprising a first liquid and a second liquid. The first liquid contains at least one organic compound in a sufficient amount to make a morphological difference among leucocytes by combining with a cationic component in leucocytes. The second liquid contains at least one ionic surfactant in a sufficient amount to be able to lyse erythrocytes and cause damage to a part of the cell membrane of leucocytes. The first and second liquid contain a nonionic surfactant and a buffer for adjusting pH. Like a single liquid type, the liquids may contain the alcohol and the metal salt. Concentration of each of the components is made so that, when the first and the second liquids are mixed, the above-mentioned concentration for each of the components results. The reagent composed of the two liquids may be improved as to its stability in storage.

The reagent may be used by mixing with whole blood. In that case, the mixing ratio of the reagent to the whole blood is in a range from 1:2 to 1:100 by volume. Incidentally, the blood sample diluted with a suitable diluent can also be used.

Figure 21:
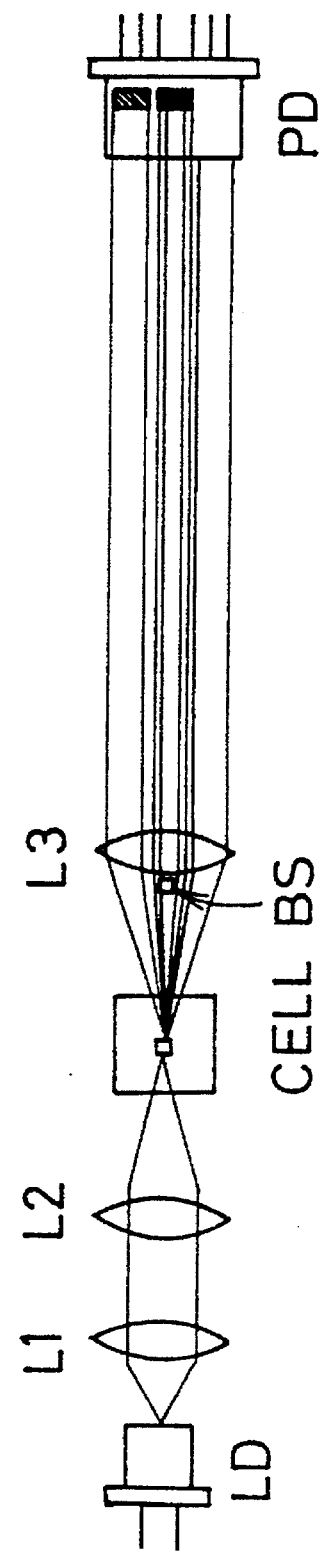
FIG. 21 is an outline chart of an apparatus for measuring the samples treated with the reagent for analyzing leucocytes of the present invention.

Using the reagent for analyzing leucocytes in accordance with the present invention, the classification and counting of leucocytes can be suitably carried out especially with a small analyzing apparatus using a semiconductor laser. That is, the reagent can be suitably used by means of an apparatus wherein leucocytes can be classified/counted only by receiving the two parameters of forward low-angle and high-angle scattered light. There is no particular limitation for the analyzing apparatus and, for example, an apparatus equipped with a simple detecting part as shown in FIG. 21 may be used. The apparatus of FIG. 21 is equipped with a device which detects a two-angle forward scattered light. That is, in the apparatus of FIG. 21, there is a semiconductor laser LD before the flow cell CELL via a contender lens L2 and a collimater lens L1. Further, there is a photodiode PD after the flow cell CELL via a collector lens L3 equipped with a beam stopper BS. In the apparatus, the intensity of the scattered light of low angles (about 1°–5°) and high angles (about 6°–20°) among the forward scattered light is measured, and by means of the difference among the intensity of the scattered light, leucocytes can be classified into at least four subgroups and counted.

By the reagent of the present invention, leucocytes can be conveniently classified/counted using a flow cytometer.

In accordance with the reagent of the invention:

(1) the ionic surfactant may lyse erythrocytes in whole blood, damage the cell membrane of leucocytes and accelerate the permeability of an organic compound through the cell membrane;

(2) the organic compound mat adjust the morphology of the leucocytes in such a manner that is convenient for classifying leucocytes;

(3) the nonionic surfactant may solubilize an insoluble substance formed by combining of the ionic surfactant with the organic compound; and (4) the buffer may keep pH of the reagent to a certain value.

Ionic surfactants usually hemolyze erythrocytes and dissolve the cell membrane of leucocytes to make their nuclei naked. Therefore, the method of classifying leucocytes into three subgroups by determining the volume information of them has already been used widely as a simple and convenient means for classifying leucocytes. However, in this method, the hemolytic action is so strong that most of leucocytes are made naked whereby it is not possible to morphologically classify leucocytes into subtypes. On the other hand, the reagent of the present invention utilizes fundamentally the same principle of the action of the ionic surfactant as in the above mentioned method, i.e., the ionic surfactant lyses erythrocytes and damages the membrane of leucocytes. However, the hemolytic action required in the reagent of the present invention is to disrupt a part of the cell membrane, possibly a part of the lipid components, resulting in the formation of pores in erythrocytes which can pass hemoglobin forming small pores in leucocytes which can pass an organic compound, while the nucleus of leucocytes is not naked. As a result, hemoglobin is dispersed out of the erythrocytes whereby the erythrocytes hardly scatter the light whereupon they can be discriminated from leucocytes by optical information. As a result of a partial flowing-out of cell membrane and the liquid of the leucocytes, the partly-damaged leucocytes significantly reduce the light scattering from the cell surface whereby information in the cells can be obtained in more detail.

It has been well known that the ionic surfactant increases its solubilizing ability, depending upon the concentration at the concentration higher than the CMC of the surfactant. In the conventional method, leucocytes are made naked using the above-mentioned solubilizing ability of the surfactant, while, in the present invention, the ionic surfactant is used in a low concentration and, therefore, the solubilizing ability of the ionic surfactant is low whereby, quite unexpectedly, the positive charge in the ionic surfactant neutralizes the negative charge of anionic components (nuclei, granules, RNA, etc.) in the cells to make them insoluble. As a result, even when leucocytes are treated with the ionic surfactant, the shape of the cells hardly changes whereby the effect of keeping the cell shape which is similar to that achieved by fixing the cell by an aldehyde can result. Consequently, the reagent of the present invention does not have an influence on an analytical result by change of treating conditions as period and temperature. The reagent of the present invention is thus different from the known method for classifying leucocytes into three subgroups by use of the ionic surfactant. A sample treated with the reagent of the present invention is stable for a long period.

Furthermore, the organic compound acts to insolubilize the cationic component in leucocyte cells (e.g. granules [eosinophilic granules], protein, etc.) whereby a similar effect as of fixing with an aldehyde is obtained and, probably, the morphological difference (e.g. a difference in the scattered light) is made among leucocytes depending upon the amount of the cationic component. In other words, it is likely that, as a result of a neutralization of the positive charge of the cationic component in the cells to make them insoluble, their flowing-out of the cells can be inhibited, the morphological information of leucocytes is maintained and the shape of leucocytes can be changed so as to be convenient for the classification.

In the present invention, the nonionic surfactant is used to solubilize the insoluble substance which is produced by a combination of the ionic surfactant with the organic compound.

Furthermore, in the present invention, the presence of the ionic surfactant in a small amount inhibits an excessive solubilization.

In the present invention, though the alcohol is not always necessary, if added, it is effective in terms of the following respects. The alcohol selectively potentiates the action of an ionic surfactant whereby the ionic surfactant even in a low concentration can cause damage to the cell membrane. In addition, it is likely that the alcohol denatures proteins contained in the cell to make it insoluble. Accordingly, when the alcohol is used, it is possible that the damage of the cell such as the loss of the cell membrane and granules is kept to a minimum and consequently that the desired damage of the cell membrane is caused. Therefore, the alcohol has an effect of maintaining the optical difference by the scattered light, etc. Moreover, the alcohol exhibits an action of accelerating the lysis of erythrocytes. Therefore, even though the membrane of erythrocytes is difficult to lyse in some diseases such as cirrhosis, the addition of the alcohol is effective in such a case, in turn, erythrocytes are lysed and the damage of leucocytes is inhibited. It is probable that the alcohol hurts the cell membrane of erythrocytes by a mechanism different from that of the ionic surfactant.

Preferred reagents of the reagent for analyzing leucocytes in accordance with the present invention will be given as hereunder.

EXAMPLE 1

| | |
|---|---|
| Ionic surfactant | 100–500 mg |
| Magnesium 8-anilino-1-naphthalenesulfonate (an organic compound) | 2 g |
| BC30TX (a nonionic surfactant: polyoxyethylene (30) cetyl ether; Nikko Chemicals) | 1 g |
| HEPES | 10 mM |
| Methanol | 100 ml |
| NaOH | sufficient for pH 7.0 |
| Distilled water | q.s. to 1000 ml |

The reagent (1 ml) of the above-mentioned composition in which various kinds of surfactants in various concentrations were used as an ionic surfactant was mixed with 30 microliters of blood and, after 30 seconds, the forward low-angle scattered light and the forward high-angle scattered light were measured using a flow cytometer.

FIGS. 1–4 show the results wherein 750 mg/liter of decyltrimethylammonium bromide (DTAB), 500 mg/liter of lauryltrimethylammonium chloride, 500 mg/liter of myristyltrimethylammonium bromide and 100 mg/liter of cetyltrimethylammonium chloride were used as the ionic surfactant, respectively. In the drawings, L is lymphocyte, M is monocyte, N is neutrophil and basophil and E is eosinophil. For all of the ionic surfactants, nearly the same scattergrams were resulted whereby leucocytes were able to be classified and counted.

EXAMPLE 2

| | |
|---|---|
| DTAB (a cationic surfactant) | 1.5 g |
| An organic compound | 0.3–3 g |
| BC30TX (a nonionic surfactant; Nikko Chemicals) | 1 g |
| Citric acid | 50 mM |
| Methanol | 100 ml |
| NaOH | sufficient for pH 7.5 |
| Distilled water | q.s. to 1000 ml |

The reagent (1 ml) of the above-mentioned composition in which various kinds of organic compounds in various concentrations were used as the organic compound was mixed with 30 microliters of blood and, after 30 seconds, the forward low-angle scattered light and the forward high-angle scattered light were measured using a flow cytometer.

FIGS. 5–8 show the results where 3 g/liter of Alizaline Violet 3R, 0.3 g/liter of Alphazurine A, 0.3 g/liter of Guinea Green B and 3 g/liter of Alizarin Yellow R were used, respectively. For all of the organic compounds used, nearly the same scattergrams were obtained whereby the leucocytes were able to be classified and counted.

EXAMPLE 3

| | |
|---|---|
| DTAB | 1.5 g |
| Brilliant Crocein M00 (an organic compound) | 1 g |
| HEPES | 10 mM |
| HCO50 (a nonionic surfactant; polyoxyethylene (50) hydrogenated castor oil; Nikko Chemicals) | 4 g |
| Alcohol | q.s. |
| NaOH | sufficient for pH 7.0 |
| Distilled water | q.s. to 1000 ml |

The reagent (1 ml) of the above-mentioned composition in which various kinds of alcohols in various concentrations were used as the alcohol was mixed with 80 microliters of blood and, after 30 seconds, the forward low-angle scattered light and the forward high-angle scattered light were measured using a flow cytometer.

FIGS. 9–12 show the results when 100 ml/liter of methyl alcohol, 50 ml/liter of ethyl alcohol, 25 ml/liter of 2-propanol and 2.5 ml/liter of 2-phenoxyethanol were used as the alcohol, respectively. The erythrocytes were well contracted when any of the alcohols was used whereby the leucocytes were able to be counted giving nearly the same scattergrams. Thus, the leucocytes were able to be classified and counted.

EXAMPLE 4

| | |
|---|---|
| DTAB | 1.5 g |
| Magnesium 8-anilino-1-naphthalenesulfonate (an organic compound) | 2 g |
| HCO50 (a nonionic surfactant; Nikko Chemicals) | 4 g |
| Buffer | 10 mM |
| 2-Phenoxyethanol | 2.5 ml |
| NaOH | q.s. |
| Distilled water | q.s. to 1000 ml |

The reagent (1 ml) of the above-mentioned composition in which various kinds of buffers in various concentration were used for changing pH was mixed with 30 microliters of blood and, after 30 seconds, the forward low-angle scattered light and the forward high-angle scattered light were measured using a flow cytometer.

Figure 13:
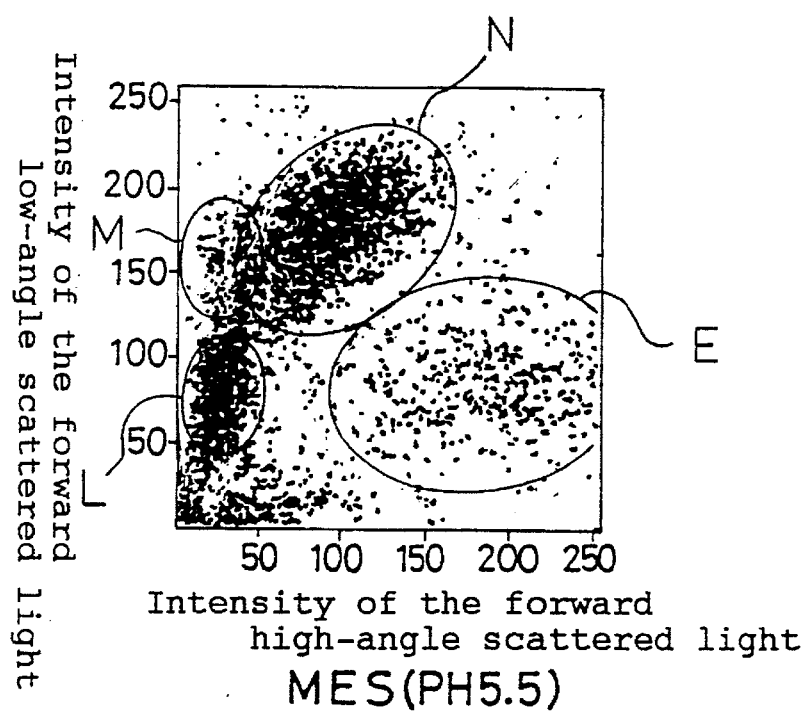
FIG. 13 is a scattergram showing the intensity of forward low-angle scattered light and the intensity of forward high-angle scattered light measured with the reagent for analyzing leucocytes of the present invention which uses MES as a buffer.
Figure 14:
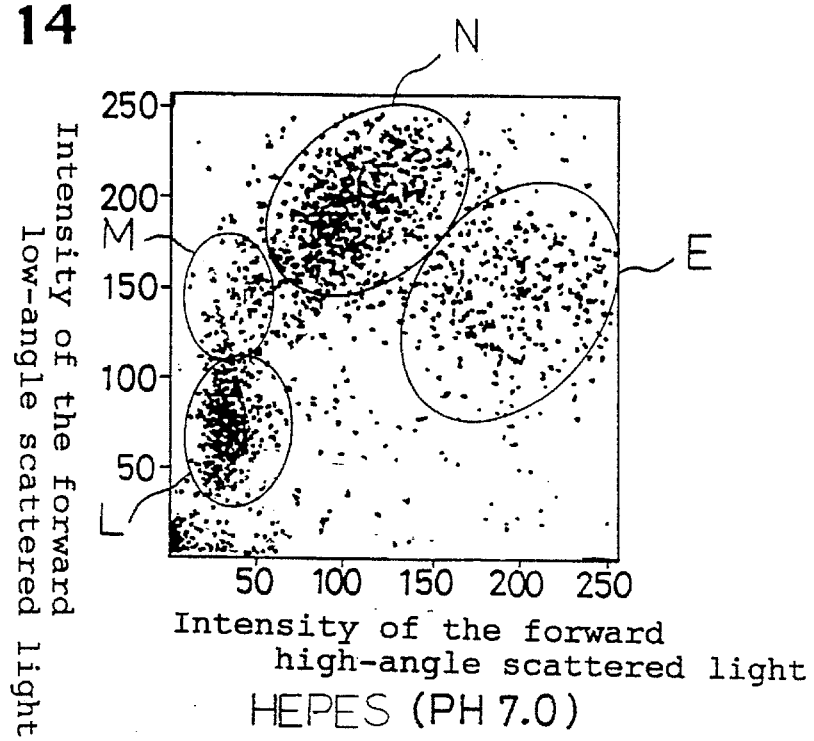
FIG. 14 is a scattergram showing the intensity of forward low-angle scattered light and the intensity of forward high-angle scattered light measured with the reagent for analyzing leucocytes of the present invention which uses HEPES as a buffer.
Figure 15:
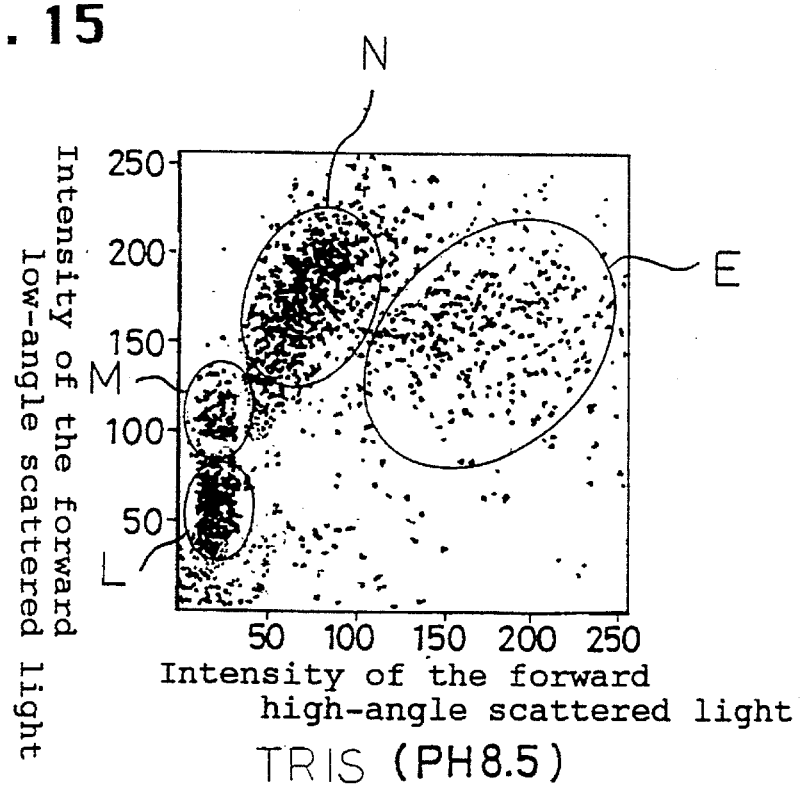
FIG. 15 is a scattergram showing the intensity of forward low-angle scattered light and the intensity of forward high-angle scattered light measured with the reagent for analyzing leucocytes of the present invention which uses TRIS as a buffer.

FIGS. 13–15 show the results where MES (pH: 5.5), HEPES buffer (pH: 7.0) and TRIS buffer (pH: 8.5) were used, respectively. Though there was a tendency of the intensity of the scattered light of the leucocytes to decreased as pH of the reagent goes up, it was still possible to classify and count the leucocytes.

EXAMPLE 5

| | |
|---|---|
| DTAB | 1.0 g |
| Magnesium 8-anilino-1-naphthalenesulfonate (an organic compound) | 1.5 g |
| BC-25TX (a nonionic surfactant; polyoxyethylene (25) cetyl ether; Nikko Chemicals) | 4 g |
| HEPES | 10 mM |
| Methanol | 100 ml |
| NaOH | sufficient for pH 7.0 |
| Distilled water | q.s. to 1000 ml |

The reagent (1 ml) of the above-mentioned composition was mixed with 30 microliters of blood and, after 30 seconds, the forward low-angle scattered light and the forward high-angle scattered light were measured using a flow cytometer.

Figure 16:
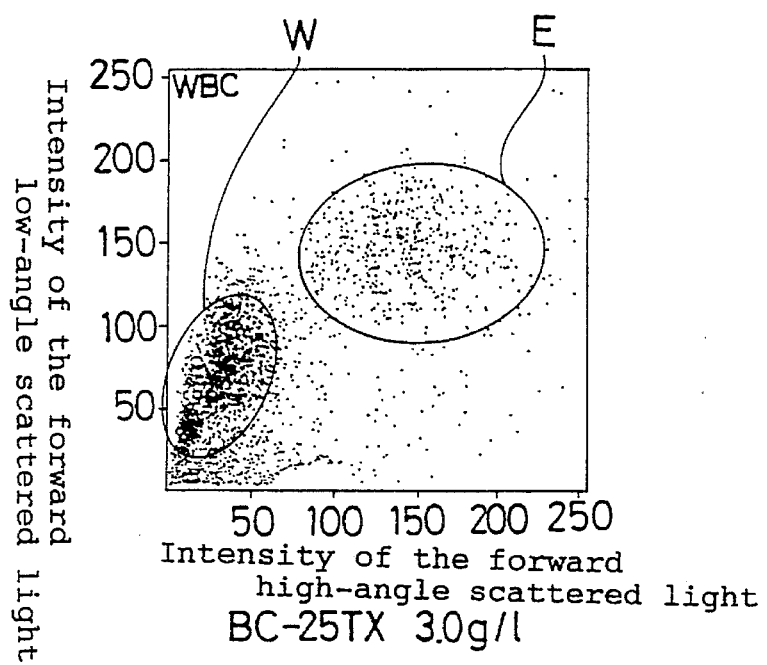
FIG. 16 is a scattergram showing the intensity of forward low-angle scattered light and the intensity of forward high-angle scattered light measured with the reagent for analyzing leucocytes of the present invention which uses BC-25TX as a nonionic surfactant.

FIG. 16 shows the result where 3.0 g/liter of BC-25TX was added as a nonionic surfactant for solubilizing the precipitate formed by a combination of the components for constituting erythrocytes with the ionic surfactant. In FIG. 16, not only the effect of solubilizing the precipitate but also the influence on the leucocytes was noted. Thus, among the leucocytes, those (w) which were other than the eosinophils were contracted whereby it was not possible to classify them into four groups.

Figure 17:
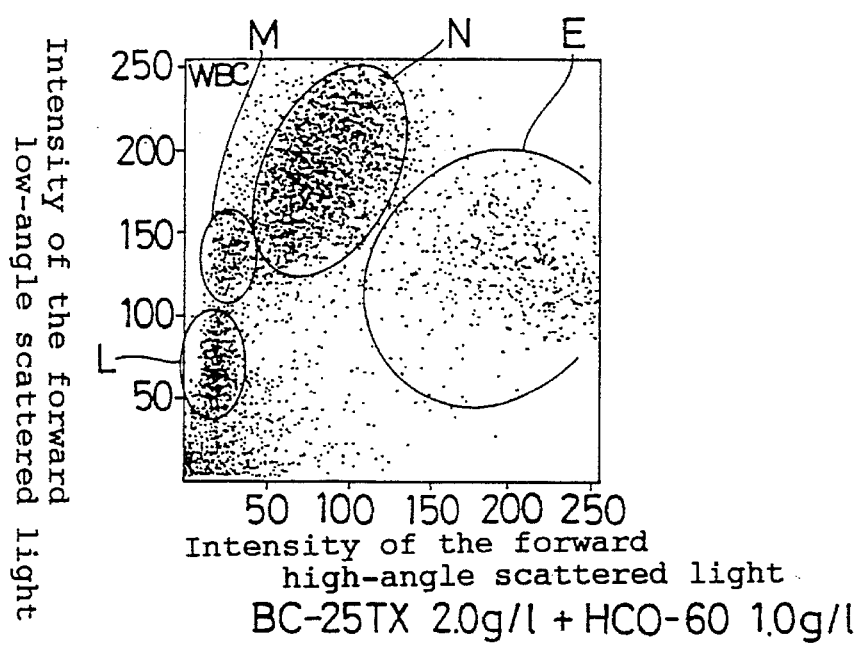
FIG. 17 is a scattergram showing the intensity of forward low-angle scattered light and the intensity of forward high-angle scattered light measured with the reagent for analyzing leucocytes of the present invention which uses BC-25TX and HCO-60 are jointly used as a nonionic surfactant.

Now, the nonionic surfactant used (i.e. BC-25TX) was reduced to 2.0 g/liter and 1.0 g/liter of HCO-60 (Nikko Chemicals; additional mole number of polyoxyethylene was 60) which was a type of polyoxyethylene hydrogenated castor oil was added thereto whereby the result was that, as shown in FIG. 17, no precipitate was produced and a good scattergram classifying the leucocytes into four groups was achieved.

EXAMPLE 6

| | |
|---|---|
| DTAB | 1.5 g |
| Magnesium 8-anilino-1-naphthalenesulfonate (an organic compound) | 2 g |
| HCO 50 (a nonionic surfactant; polyoxyethylene (50) hydrogenated castor oil; Nikko Chemicals) | 4 g |

| | |
|---|---|
| PEN 4630 (a nonionic surfactant; polyoxyethylene (30) polyoxypropylene (6) 2-decyl tetradecyl ether; Nikko Chemicals) | 4 g |
| Phthalic acid | 50 mM |
| 2-Phenoxyethanol | 2.5 ml |
| NaOH | sufficient for pH 5.5 |
| NaCl | 30 mM |
| Distilled water | q.s. to 1000 ml |

One ml of the reagent of the above composition and 30 microliters of blood were mixed and, after 30 seconds, a measurement was conducted using a flow cytometer.

Figure 18:
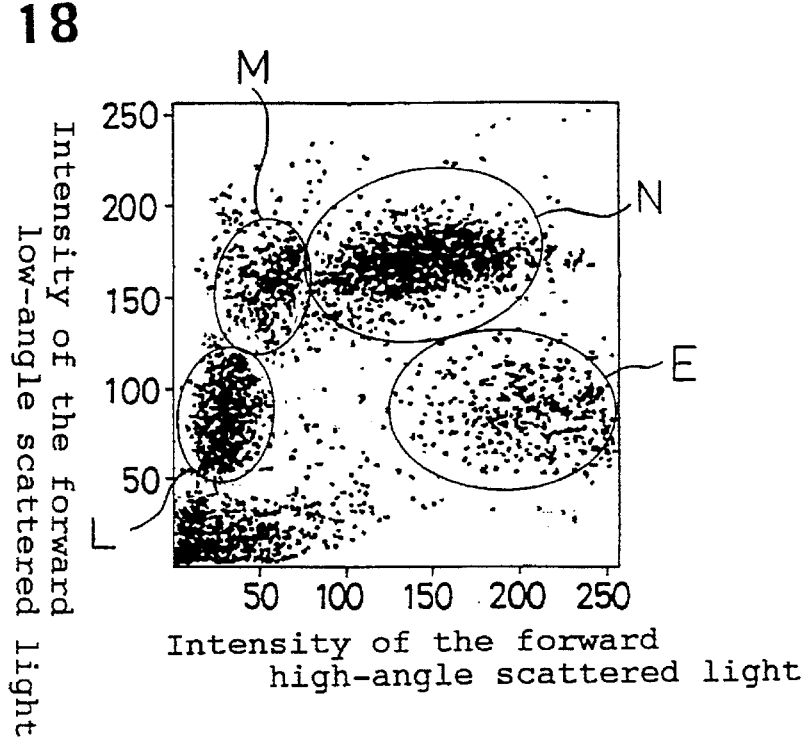
FIG. 18 is a scattergram showing the intensity of forward low-angle scattered light and the intensity of forward high-angle scattered light measured with the reagent for analyzing leucocytes of the present invention.
Figure 19:
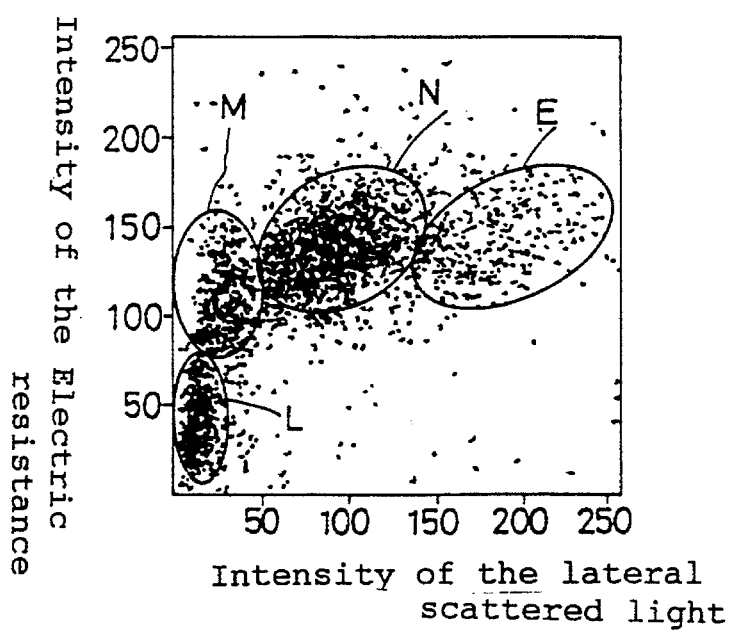
FIG. 19 is a scattergram showing the volume on the principle of measuring electric resistance and the intensity of side scattered light measured with the reagent for analyzing leucocytes of the present invention.

FIG. 18 shows the result of the measurement of forward low-angle scattered light for determining the size information and also the result of the measurement of forward high-angle scattered light for determining the morphological information. Furthermore, FIG. 19 shows the results of measuring the lateral scattered light for determining the morphological information and of measuring the volume by a principle of measurement by means of an electric resistance for determining the size information using a flow cytometer whereby the electric resistance signals were able to be measured as disclosed in the Japanese Laid-Open Patent Publication Hei-05/034,251.

In the above-mentioned reagent composition the electro-conductivity of the sample to be measured was adjusted to a suitable value by adding sodium chloride thereto for measurement on the principle of electric resistance.

The leucocytes were able to be clearly classified and counted by any of the measuring parameters.

EXAMPLE 7

A first liquid

| | |
|---|---|
| Ammonium 8-amilino-1-nathphalenesulfonate (an organic compound) | 3.0 g |
| HCO 50 (a nonionic surfactant; polyoxyethylene (50) hydrogenated castor oil; Nikko Chemicals) | 5 g |
| PEN 4630 (a nonionic surfactant; polyoxyethylene (30) polyoxypropylene (6) 2-decyl tetradecyl ether; Nikko Chemicals) | 1.3 g |
| Phthalic acid | 2.5 g |
| Succinic acid 2Na 6H$_2$O | 13.5 mg |
| 2-Phenoxyethanol | 4.7 ml |
| NaOH | sufficient for the pH 5.3 |
| NaCl | 2.9 g |
| Distilled water | q.s. to 1000 ml |

A second liquid

The second liquid had the same composition and concentration as the first liquid except that DTAB 6.9 g/liter was used in place of ammonium 8-anilino-1-nathphalene-sulfonate.

One ml of the first liquid of the above composition and 33 μl of blood were mixed, then 0.2 ml of the second liquid was added, and a mixture was reacted for 20 seconds at 35° C., followed by measuring the forward low-angle scattered light and the forward high-angle scattered light with a flow cytometer.

Figure 20:
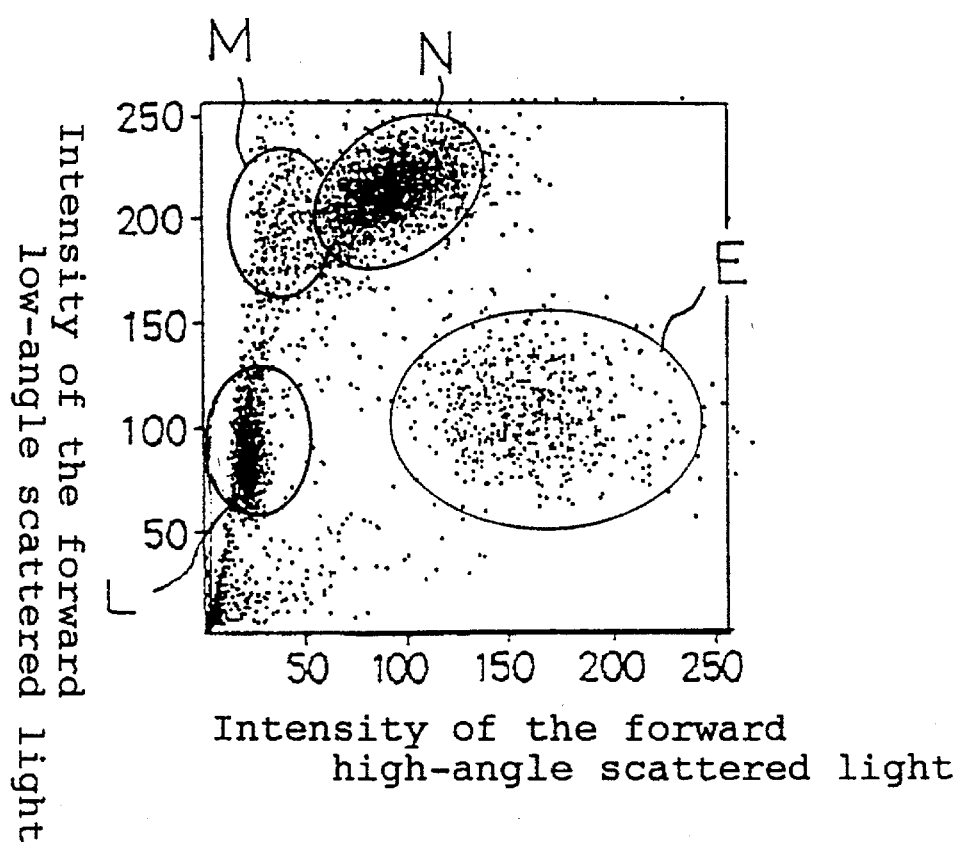
FIG. 20 is a scattergram showing the intensity of forward low-angle scattered light and the intensity of forward high-angle scattered light measured with the reagent for analyzing leucocytes of the present invention.

FIG. 20 shows the result. When the reagent consisted of the first and second liquids, a good scattergram was obtained whereby the leucocytes were able to classified into four and counted.

As illustrated hereinabove, it is now possible with the present invention to provide a reagent composition which substantially comprises one aqueous solution and can be used for classifying and counting leucocytes by a simple procedure of just mixing the reagent of the present invention with a blood sample. Accordingly, classification of leucocytes can be conducted by only measuring two scattered light signals and an apparatus of a simple structure can be applied.

In addition, there is no need for using dangerous chemicals such as an aldehyde and, therefore, it is now possible to classify and count blood samples safely.

We claim:

1. A reagent for analyzing leucocytes comprising
   (a) at least one ionic surfactant, being either a cationic or an amphoteric surfactant, in an amount sufficient for lysing erythrocytes and causing damage to a part of cell membranes of leucocytes;
   (b) at least one organic compound having a hydrophobic group and an acidic group which has a negative charge in an aqueous solution in an amount sufficient for preserving leucocyte morphology by combining with a cationic component in leucocytes;
   (c) a nonioinic surfactant; and
   (d) a buffer for adjusting pH.

2. A reagent according to claim 1 in which the reagent further contains an alcohol.

3. A reagent according to claim 2 in which the alcohol is methanol, ethanol, propanol or 2-phenoxy ethanol.

4. A reagent according to claim 1 or 2 in which the reagent further contains a metal salt.

5. A reagent according to claim 4 in which the metal salt is sodium chloride, potassium chloride or lithium chloride.

6. A reagent according to claim 1 in which the ionic surfactant is at least one cationic surfactant represented by the formula;

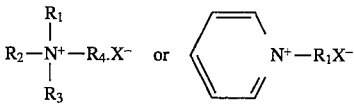

wherein $R_1$ is a $C_{6-18}$ alkyl or alkenyl group; $R_2$ and $R_3$ are $C_{1-4}$ alkyl or alkenyl groups; $R_4$ is a $C_{1-4}$ alkyl or alkenyl group or a benzyl group; and X is a halogen atom.

7. A reagent according to claim 1 in which the ionic surfactant is at least one amphoteric surfactant represented by the formula;

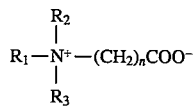

wherein $R_1$ is a $C_{6-18}$ alkyl or alkenyl group; $R_2$ and $R_3$ are $C_{1-4}$ alkyl or alkenyl groups; $R_4$ is a $C_{1-4}$ alkyl or alkenyl group or a benzyl group; and X is a halogen atom.

8. A reagent according to claim 1 in which the organic compound has at least six carbon atoms.

9. A reagent according to claim 8 in which the organic compound is at least one substance selected from the group consisting of 8-anilino-1-naphthlenesulfonic acid or salts thereof, 6-(p-toluidino)-2-naphthalenesulfonic acid or salts thereof, chromotropic acid, phthalic acid, naphthalenesulfonic acid and acidic dyes.

10. A reagent according to claim 9 in which the acidic dyes are Brilliant Crocein MOO, Alizaline Violet 3R, Alphazurine A, Guinea Green B, and Alizarin Yellow R.

11. A reagent according to claim 1 in which a hydrophilic group of the nonionic surfactant is selected from the group consisting of polyoxyethylene glycol, polypropylene glycol and polyoxyethylene glycol-polyoxypropylene glycol block copolymer.

12. A reagent according to claim 11, wherein said at least one nonionic surfactant is selected from the group consisting of polyoxyethylene (50) hydrogenated castor oil, polyoxyethylene (60) hydrogenated castor oil, polyoxyethylene (25) cetyl ether, polyoxyethylene (30) cetyl ether, and polyoxyethylene (30) polyoxypropylene (6) 2-decyl tetradecyl ether.

13. A reagent according to claim 12, wherein said at least one nonionic surfactant comprises polyoxyethylene (60) hydrogenated castor oil and polyoxyethylene (30) cetyl ether or polyoxyethylene (50) hydrogenated castor oil and polyoxyethylene (30) polyoxypropylene (6) 2-decyl tetradecyl ether.

14. A reagent according to claim 1 in which two or more nonionic surfactants are used.

15. A reagent according to claim 1 in which the nonionic surfactant is contained in about 30–5,000 mg per liter of the reagent.

16. A reagent according to claim 1 in which the organic compound used is contained in about 50–5,000 mg per liter of the reagent.

17. A reagent according to claim 1 in which the reagent is composed of two liquids comprising a first liquid containing the at least one organic compound, and a second liquid containing the at least one ionic surfactant, the first and the second liquid further containing a nonionic surfactant and a buffer for adjusting pH.

18. A reagent according to claim 1 in which the reagent is mixed with blood in the range from 1:2 to 1:100 by volume.

19. A reagent for analyzing leucocytes according to claim 1, in which the ionic surfactant comprises at least one cationic surfactant represented by the formula;

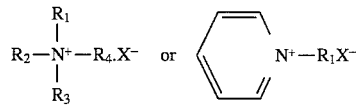

wherein $R_1$ is a $C_{6-18}$ alkyl or alkenyl group; $R_2$ and $R_3$ are $C_{1-4}$ alkyl or alkenyl groups; $R_4$ is a $C_{1-4}$ alkyl or alkenyl group or a benzyl group; and X is a halogen atom; or at least one amphoteric surfactant represented by the formula;

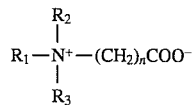

wherein $R_1$ is a $C_{6-18}$ alkyl or alkenyl group; $R_2$ and $R_3$ are $C_{1-4}$ alkyl or alkenyl groups; $R_4$ is a $C_{1-4}$ alkyl or alkenyl group or a benzyl group; and X is a halogen atom; and wherein the organic compound is selected from the group consisting of an acid dye and an aromatic organic acid having a hydrophobic group comprising an acidic functional group and either a heterocyclic ring or a hydrocarbon of at least six carbon atoms.

20. A reagent for treating a blood sample for analysis of leucocytes comprising a first liquid and a second liquid, wherein said first liquid comprises at least one organic compound selected from the group consisting of 8-anilino-1-naphthalenesulfonic acid, a salt of 8-anilino-1-naphthalenesulfonic acid, 6-(p-toluidino)-2-naphthalenesulfonic acid, a salt of 6-(p-toluidino)-2-naphthalenesulfonic acid, chromotropic acid, phthalic acid, naphthalenesulfonic acid, Amido Black, Alizarin Cyanine Green F, Acid Green 27, Acid Blue 62, Direct Red 31, Brilliant Sulfaflavine, Alizarin Yellow R, Acid Blue 129, Acid Green 25, Chromotrope 2R, Coomassie Brilliant Blue R-250, Carmine Acid, Coomassie Brilliant Blue G-250, Carmoisine B, Direct Blue 86, 2-(4-diethylaminophenylazo)benzoic acid, Para Rosaniline, Violamine R, Acid Yellow 34, Acid Orange 51, Brilliant Crocein MOO, Guinea Green B, Acid Blue 29, Rhodamine B, Sulforhodamine B, Lissamine Green B, Acid Blue 9, Fast Green FCF, Azocarmine B, Aniline Blue, Alphazurine A, Alizaline Violet 3R, Acid Blue 41, Bieblich Scarlet, Erythrosin B, Methyl Red, Methyl Orange, and Orange I, wherein said organic compound is present in an amount effective for preserving leucocyte morphology by combining with a cationic component in leucocytes;

and wherein said second liquid comprises at least one ionic surfactant, being either a cationic or an amphoteric surfactant in an amount effective for lysing erythrocytes and damaging the cell membrane of leucocytes while not making the nuclei of said leucocytes naked;

and wherein each of said first and second liquids further comprise a nonionic surfactant and a buffer.

21. A reagent according to claim 20, wherein said at least one nonionic surfactant is selected from the group consisting of polyoxyethylene (50) hydrogenated castor oil, polyoxyethylene (60) hydrogenated castor oil, polyoxyethylene (25) cetyl ether, polyoxyethylene (30) cetyl ether, and polyoxyethylene (30) polyoxypropylene (6) 2-decyl tetradecyl ether.

22. A reagent according to claim 21, wherein said at least one nonionic surfactant comprises polyoxyethylene (60) hydrogenated castor oil and polyoxyethylene (30) cetyl ether or polyoxyethylene (50) hydrogenated castor oil and polyoxyethylene (30) polyoxypropylene (6) 2-decyl tetradecyl ether.

23. A reagent for treating a blood sample for analysis of leucocytes comprising:

i) at least one ionic surfactant, being either a cationic or an amphoteric surfactant, in an amount sufficient effective for lysing erythrocytes and damaging a part of cell membranes of leucocytes;

ii) at least one organic compound having a hydrophobic group and an acidic group which has a negative charge in an aqueous solution, wherein said organic compound is present in an amount effective for preserving leucocyte morphology by combining with a cationic component in leucocytes;

iii) at least one nonionic surfactant selected from the group consisting of polyoxyethylene (50) hydrogenated castor oil, polyoxyethylene (60) hydrogenated castor oil, polyoxyethylene (25) cetyl ether, polyoxyethylene

(30) cetyl ether, and polyoxyethylene (30) polyoxypropylene (6) 2-decyl tetradecyl ether; and iv) a buffer for adjusting pH.

24. A reagent according to claim 23, which further comprises an alcohol.

25. A reagent according to claim 23, which further comprises an alkali metal salt.

26. A reagent according to claim 23 in which the ionic surfactant is at least one cationic surfactant represented by the formula

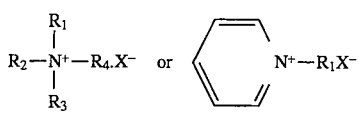

wherein $R_1$ is a $C_{6-18}$ alkyl or alkenyl group; $R_2$ and $R_3$ are $C_{1-4}$ alkyl or alkenyl groups; $R_4$ is a $C_{1-4}$ alkyl or alkenyl group or a benzyl group; and X is a halogen atom.

27. A reagent according to claim 23 in which the ionic surfactant is at least one amphoteric surfactant represented by the formula;

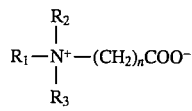

wherein $R_1$ is a $C_{6-18}$ alkyl or alkenyl group; $R_2$ and $R_3$ are $C_{1-4}$ alkyl or alkenyl groups; $R_4$ is a $C_{1-4}$ alkyl or alkenyl group or a benzyl group; and X is a halogen atom.

28. A reagent according to claim 23, wherein said at least one nonionic surfactant comprises polyoxyethylene (60) hydrogenated castor oil and polyoxyethylene (30) cetyl ether or polyoxyethylene (50) hydrogenated castor oil and polyoxyethylene (30) polyoxypropylene (6) 2-decyl tetradecyl ether.

\* \* \* \* \*